United States Patent [19]

Buchheister et al.

[11] Patent Number: 5,236,330
[45] Date of Patent: Aug. 17, 1993

[54] EXHAUST MEASURING EQUIPMENT

[75] Inventors: Hasso Buchheister; Louis Lorentz, both of Mannheim, Fed. Rep. of Germany

[73] Assignee: Motoren-Werke Mannheim AG, Mannheim, Fed. Rep. of Germany

[21] Appl. No.: 788,566

[22] Filed: Nov. 6, 1991

[30] Foreign Application Priority Data

Nov. 6, 1990 [DE] Fed. Rep. of Germany ....... 4035173

[51] Int. Cl.[5] ........................................... F02M 25/06
[52] U.S. Cl. .................................. 60/276; 60/278; 123/568
[58] Field of Search ................ 60/276, 278; 123/571, 123/568

[56] References Cited

U.S. PATENT DOCUMENTS 3,885,540  5/1975  Stadler ........................ 123/568
4,617,795 10/1986  Abthoff ........................ 60/276

*Primary Examiner*—Douglas Hart
*Attorney, Agent, or Firm*—Charles L. Schwab

[57] ABSTRACT

This invention relates to an exhaust gas measuring device, in particular for the measurement of the oxygen content in the exhaust gas stream of an internal combustion engine, which device can be connected to an exhaust gas line, having a measuring device arranged in an insulation, to which measuring device a measuring probe is connected, which is led out of the insulation.

7 Claims, 1 Drawing Sheet

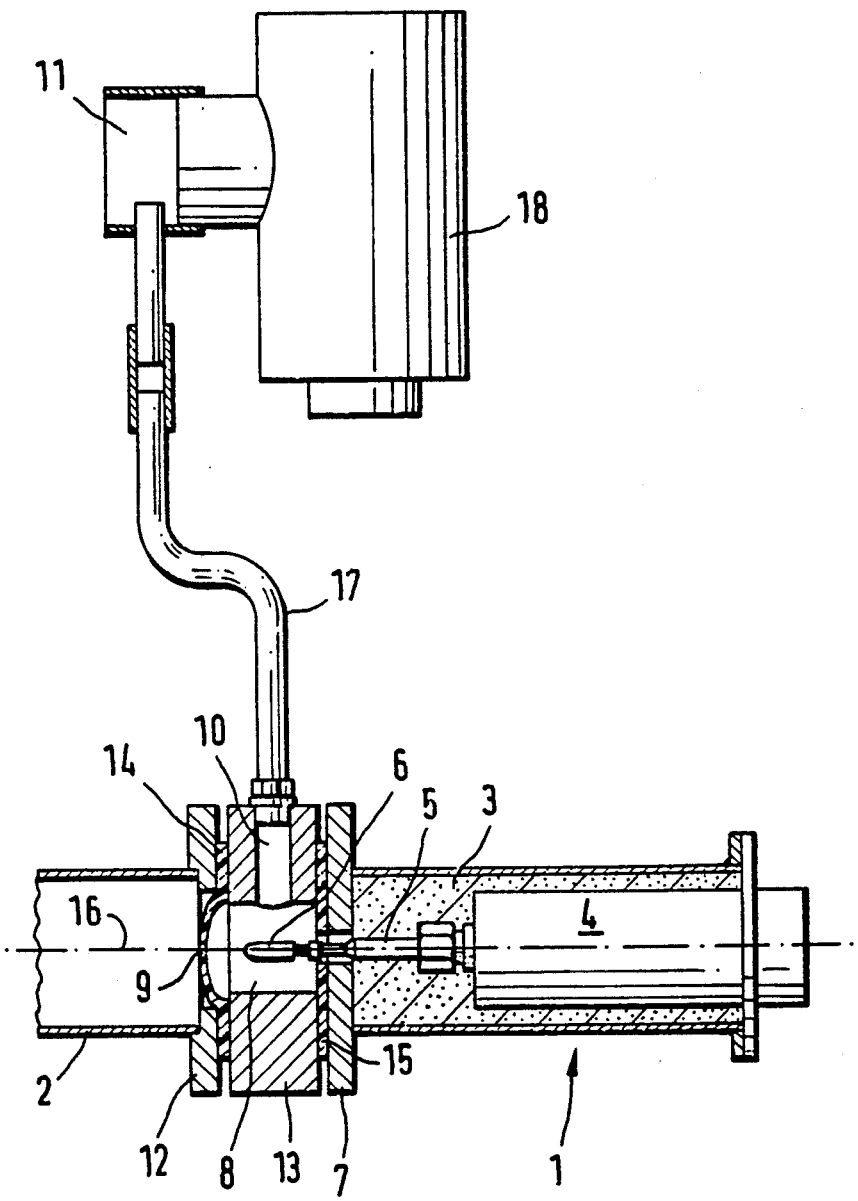

EXHAUST MEASURING EQUIPMENT

TECHNICAL FIELD

This invention relates to an exhaust gas measuring device, in particular for the measurement of the oxygen content in the exhaust gas stream of an internal combustion engine.

PRIOR ART STATEMENT

For the control of an internal combustion engine, in particular a gasoline engine, the state of the art is to employ the oxygen content of the exhaust gas as a control/regulation quantity. For this purpose there are exhaust gas measuring devices that can be connected to the exhaust gas line of the internal combustion engine. Said exhaust gas measuring devices consist of a measuring device and of a measuring probe connected to said measuring device, which measuring probe extends into the exhaust gas stream to be measured. For the connection of the exhaust gas measuring probe to the exhaust gas line, a separable connecting element (flange) is attached to each of the exhaust gas line and the exhaust gas measuring probe. In the operation of this exhaust gas measuring device, deviations of the measured values have come about, which deviations are independent of the oxygen content of the exhaust gas. These deviations lead to intolerable errors in the control/regulation of the internal combustion engine. Pressure and temperature fluctuations of the exhaust gas have revealed themselves as error quantities.

OBJECTS AND SUMMARY OF THE INVENTION

It is the object of invention create exhaust gas measuring device, whose measurement results are almost independent of pressure and temperature fluctuations of the exhaust gas.

By virtue of the fact that a measuring space is arranged between the exhaust gas line and the exhaust gas measuring device, which measuring space exhibits a throttled gas inlet opening to the exhaust gas line and a gas outlet opening, which is connected to a space in which a lower pressure prevails than in the exhaust gas line, the measured values achieved by means of the exhaust gas measuring device in accordance with the invention are almost independent of pressure and temperature fluctuations of the exhaust gas.

The pressure in the space that is connected to the gas outlet opening is advantageously almost constant. This is the case if such space is the intake air line of the internal combustion engine.

The exhaust gas line and the exhaust gas measuring device is expediently connected to the vessel via flanges with seals. The term flange is generally to be understood as a separable connecting element. In order for the vessel and the exhaust gas measuring device to be thermally decoupled or isolated from the exhaust gas line as best as possible, the outside diameters of the seals, in accordance with the invention, are minimized in relation to the outside diameters of the flanges.

For further thermal decoupling, in accordance with the invention, the seal between the exhaust gas line and the vessel within the flange consists of a disk, which exhibits at least the gas inlet opening acting as a throttle. Here the gas inlet opening is selected as small as possible so that the heat flux or flow is minimized.

BRIEF DESCRIPTION OF THE DRAWINGS

Further features can be understood from the single FIGURE drawing showing one embodiment of the invention.

DETAILED DESCRIPTION OF THE DRAWINGS

The FIGURE shows an exhaust gas line 2 of an internal combustion engine or gasoline engine, not shown more closely. Connected to the exhaust gas line 2 is an exhaust gas measuring device 1 for the measurement of the oxygen content of the exhaust gas. For this purpose, the exhaust gas line 2 and the measuring device 1 each exhibit a flange 7, 12, which are connected to other via a vessel 13. Between each the two flanges 7, 12 and the vessel 13 there are jackets in the form of seals 14, 15. The measuring device 1 consists of a measuring device 4--arranged in an insulation 3--, to which a measuring probe 5 is connected, which is led out of the insulation 3 and extends into a measuring space 8 in the vessel 13. The measuring probe 5 thus penetrates the flange 7 and the seal 15. The tip 6 of the measuring probe 5 is arranged almost in the center of the measuring space 8.

The seal 14 between the exhaust gas line 2 and the vessel 13 consists of a disk, which exhibits at least one gas inlet opening 9 made as a throttle. Said gas inlet opening 9 is arranged, for example, centrally in the disk on the symmetry axis 16 of the measuring probe 5.

In order for the vessel 13 and thus also the exhaust gas measuring device to be thermally decoupled or isolated from the exhaust gas line 2, the outside diameters of the seals 14, 15 are minimized relative to the diameters of the flange 7, 12. Furthermore, the seal 14 made as a disk is formed out in the direction toward the exhaust gas line 2.

Besides the gas inlet opening 9 made as a throttle, the measuring space 8 in the vessel 13 has a gas outlet opening 10, which is connected to the intake air line 11 of the internal combustion engine via a line 17. The intake air line 11 leads, as usual, via an air filter 18 into the cylinders of the internal combustion engine. The exhaust gas is thus returned again to the motor and not led into the engine room.

With regard to the gas outlet opening 10, it is especially important that such opening is connected to a space in which a lower pressure prevails than in the exhaust gas line 2. This pressure should be almost constant.

By means of the measures just described, the heat flow and the radiation is purposely reduced to a minimum by means of the arrangement of components, by means of the number, shape and design of the seals.

We claim:

1. A combustion products gas measuring device for measuring the oxygen content in the combustion products gas stream of a combustion products pipe line (2) of an internal combustion engine, comprising: a housing (13) with a measuring cavity (8), a gasket (14) between said housing (13) and said pipe line (2) presenting a throttled gas inlet opening (9) by which combustion products gas flows from said pipe line (2) into said measuring cavity (8), a measuring mechanism (4) encased in insulation and including a measuring probe (5) extending out of said insulation and into said measuring cavity (8), and a gas outlet opening (10) connected to a space in which a lower pressure prevails than in said combustion products gas line (2).

2. The combustion products gas measuring device of claim 1, wherein the pressure in said space is almost constant.

3. The combustion products gas measuring device of claim 2, wherein said space is the intake air line (11) of said internal combustion engine.

4. The combustion products gas measuring device of claim 1, wherein said combustion products gas line (2) and said exhaust gas measuring device (1) are connected to said housing (13) by flanges (7, 12) with gaskets (14, 15).

5. The combustion products gas measuring device of claim 4, wherein said flanges and gaskets are annular and the outside diameters of said seals (14, 15) are substantially less than the outside diameters of said flanges (7, 12).

6. The combustion products gas measuring device of claim 4 wherein said gasket (14) between said flange 12 of said exhaust gas line (2) and said housing (13) includes a disk portion presenting said gas inlet opening (9) acting as a throttle.

7. A combustion products gas measuring device for measuring the oxygen content in the combustion products gas stream of a combustion products pipe line (2) of an internal combustion engine having an air inlet pipe (11), comprising: a housing (13) with a measuring cavity (8) and mounting flanges at its opposite ends, a mounting flange on said pipe line 2 secured to one of said flanges on said housing, a measuring mechanism (4) encased in insulation secured to the other of said flanges on said housing and including a measuring probe (5) extending out of said insulation and into said measuring cavity (8), said measuring cavity (8) including a throttled gas inlet opening (9) connected to said combustion products gas line (2) and a gas outlet opening (10) in said housing (13) interconnecting said cavity (8) and said air inlet pipe (11).

* * * * *